United States Patent [19]
Hamura et al.

[11] Patent Number: 5,770,666
[45] Date of Patent: Jun. 23, 1998

[54] ORGANIC TRANSITION METAL COMPOUND AND PROCESS FOR THE PREPARATION OF POLYOLEFIN USING SAME

[75] Inventors: Satoshi Hamura; Toru Yoshida; Morihiko Sato, all of Mie, Japan

[73] Assignee: Tosoh Corporation, Shinnanyo, Japan

[21] Appl. No.: 568,518

[22] Filed: Dec. 7, 1995

[30] Foreign Application Priority Data

Dec. 8, 1994 [JP] Japan ................................. 6-305102

[51] Int. Cl.$^6$ .................................................. C08F 4/643
[52] U.S. Cl. ...................... 526/134; 576/160; 576/943; 576/114; 576/133; 576/126; 556/11; 556/53; 502/103; 502/117; 502/129
[58] Field of Search ................ 556/11, 53; 526/114, 526/134, 160, 943; 502/103, 117, 129

[56] References Cited

U.S. PATENT DOCUMENTS

| | | | |
|---|---|---|---|
| 4,542,199 | 9/1985 | Kaminsky et al. | 526/160 |
| 4,769,510 | 9/1988 | Kaminsky et al. | 585/517 |
| 4,892,851 | 1/1990 | Ewen et al. | 502/104 |
| 5,334,677 | 8/1994 | Razavi et al. | 526/114 |

FOREIGN PATENT DOCUMENTS

| | | |
|---|---|---|
| 086 457 | 8/1983 | European Pat. Off. . |
| 528 041 | 2/1993 | European Pat. Off. . |
| 632 063 | 1/1995 | European Pat. Off. . |
| 673 946 | 9/1995 | European Pat. Off. . |
| 4-91095 | 3/1992 | Japan . |

OTHER PUBLICATIONS

Tetrahedron Lett. (Teleay, 00404039);80; vol. 21(7); pp. 637–640, Czech. Acad. Sci.; J. Heyrovsky Inst. Phys. Chem. Electrochem.; Prague; 121 38/2; Czech., Turecek F et al, "A regiospecific double bond shift induced by titanocene catalysts."

Z. Naturfosch., B: Chem. Sci. (Znbsen, 09320776); 93; vol. 48 (5); pp. 603–607, Univ. Ulm; Sekt. Roentgen–Elcktronenbeugung; Ulm; D–89069; Germany (DE), Thewalt U et al, "Titan(IV) Fulvalenkomplexe. Darstellung und Struktur von [CptiPh2]2(C10H8)."

J. Organomet. Chem. (Jorcai, 0022328X);86; vol. 308 (1); pp. C1–C4, Univ. Massachusetts; Dep. Chem.; Amherst; 01003, MA; USA (US), Spink W C et al, "The synthesis and reactions of fulvalenedithallium."

Curtis et al, *Organometallics* 1991, 10, 3220–3226, "Preparation of Dinuclear Zirconium Hydride Complexes Containing the Fulvalene Ligand and Their Reactions with Carbon Monoxide".

M. Bochmann et al. (1994) J Organomet Chem. 484 (1994) C10–C12.

H.H. Brintzinger et al. (1995) Angew. Chem. Int. Ed. Engl. 34, 1143–1149 and notes at 1164–1165.

*Primary Examiner*—Mark Nagumo
*Attorney, Agent, or Firm*—Oblon, Spivak, McClelland, Maier & Neustadt, P.C.

[57] ABSTRACT

A novel organic transition metal compound is disclosed, which is represented by the following formula (1):

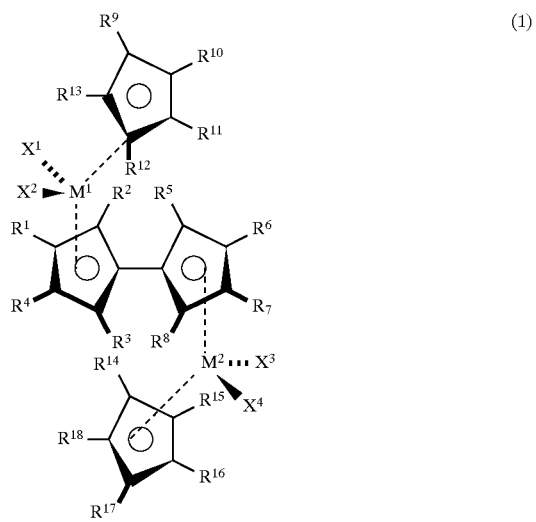

wherein the all symbols are defined in the disclosure. A polymerization catalyst comprising the organic transition metal compound and a process for the preparation of a polyolefin using the polymerization catalyst are also disclosed.

8 Claims, 3 Drawing Sheets

ORGANIC TRANSITION METAL COMPOUND AND PROCESS FOR THE PREPARATION OF POLYOLEFIN USING SAME

FIELD OF THE INVENTION

The present invention relates to a novel organic transition metal compound and a process for the preparation of a polyolefin in the presence of the organic transition metal compound as a main catalyst. More particularly, the present invention relates to an organic transition metal compound containing two transition metal atoms per molecule and having a linkage site where a part of ligands of the atoms are directly conjugated via a π bond to form a bidentate structure and a process for the preparation of a polyolefin in the presence of the organic transition metal compound as a main catalyst.

BACKGROUND OF THE INVENTION

It has been known that a "Kaminski catalyst" comprising a transition metal compound of the group 4 of the periodic table having a cyclopentadienyl derivative as a ligand (metallocene) and an aluminoxane has a high activity for the polymerization of an olefin and thus is very useful in the preparation of a polyolefin. As catalytic components for the polymerization of an olefin there have been synthesized various metallocene derivatives.

JP-A-58-19309 (The term "JP-A" as used herein means an "unexamined published Japanese patent application") (corresponding to U.S. Pat. No. 4,542,199) discloses a process for the preparation of a polyolefin in the presence of a catalyst system comprising as a catalyst component an organic transition metal compound having two cyclopentadienyl groups such as bis(cyclopentadienyl) zirconium dichloride.

JP-A-61-130314 (corresponding to U.S. Pat. No. 4,769,510) discloses a process for the preparation of an isotactic polypropylene having a high stereoregularity in the presence of, e.g., ethylenebis(4,5,6,7-tetrahydro-1- indenyl) zirconium dichloride.

JP-A-2-41303 (corresponding to U.S. Pat. Nos. 4,892,851 and 5,334,677) discloses that the use of, for example, isopropylidene (cyclopentadienyl)(fluorenyl)zirconium dichloride as a catalyst component makes it possible to prepare a syndiotactic polyolefin.

JP-A-4-91095 discloses a process for the preparation of a polyolefin in the presence of, as a catalyst component, an organic transition metal compound having two transition metal atoms per molecule obtained by crosslinking two transition metal components with a hydrocarbon group such as cyclohexanediyl, e.g., transition metal compound represented by the following formula:

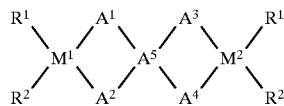

wherein $A^1$, $A^2$, $A^3$ and $A^4$ each represents a cyclopentadienyl group, a substituted cyclopentadienyl group, an indenyl group, a fluorenyl group, a substituted fluorenyl group or a derivative thereof; $A^5$ represents a $C_{4-30}$ hydrocarbondiylidene group, with the proviso that $A^1$ and $A^2$, and $A^3$ and $A^4$ are connected to the same carbon atoms in $A^5$, respectively, to form a crosslinked structure; $R^1$ and $R^2$, which may be the same or different from each other, each represents a halogen atom, a $C_{1-10}$ alkyl group or an aryl group; and $M^1$ and $M^2$, which may be the same or different from each other, each represents a metal atom selected from the group consisting of titanium, zirconium and hafnium.

However, the transition metal compound is disadvantageous in that since it has a carbon chain linkage such as $A^5$, the complex has a reduced rigidity resulting in the instability thereof. As a result of the inventors' studies, it was found that the polymerization activity provided by the use of a complex having such a carbon chain linkage as an olefin polymerization catalyst is practically insufficient.

SUMMARY OF THE INVENTION

It is therefore an object of the present invention to provide a novel and useful organic transition metal compound as a catalyst component for the polymerization of a polyolefin.

It is another object of the present invention to provide a process for the polymerization of an olefin in the presence of the foregoing organic transition metal compound.

These and other objects of the present invention will become more apparent from the following detailed description and examples.

In order to accomplish the foregoing objects of the present invention, the inventors synthesized, as a polyolefin polymerization catalyst, a novel and useful organic transition metal compound containing two transition metal atoms per molecule and having a linkage site where a part of ligands of the atoms are directly conjugated via a π bond to form a bidentate structure and made extensive studies of a process for the preparation of a polyolefin in the presence of such an organic transition metal compound as a catalyst component. Thus, the present invention has been worked out.

The present invention relates to an organic transition metal compound, represented by the following formula (1):

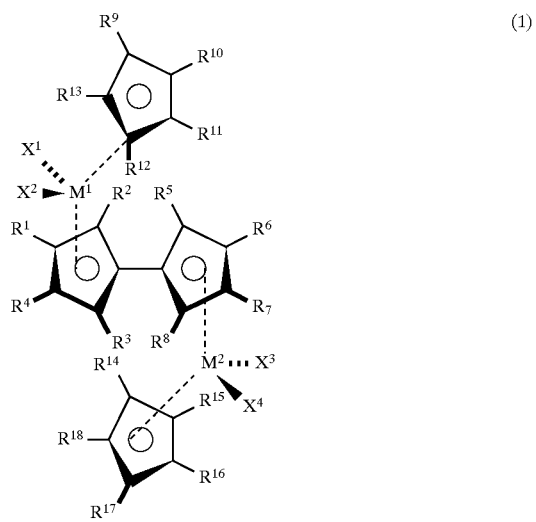

wherein $M^1$ and $M^2$, which may be the same or different from each other, each represents a transition metal atom selected from the group consisting of Ti, Zr and Hf; $R^1$, $R^2$, $R^3$, $R^4$, $R^5{}_1$, $R^6$, $R^7$ and $R^8$, which may be the same or different from each other, each represents a hydrogen atom, a $C_{1-10}$ hydrocarbon group or a $C_{1-10}$ alkylsilyl group and may be connected to each other to form rings, with the proviso that at least one of $R^1$, $R^2$, $R^3$, $R^4$, $R^5$, $R^6$, $R^7$ and $R^8$ is not a hydrogen atom; $R^9$, $R^{10}$, $R^{11}$, $R^{12}$, $R^{13}$, $R^{14}$, $R^{15}$, $R^{16}$, $R^{17}$ and $R^{18}$, which may be the same or different, each represents a hydrogen atom, a $C_{1-10}$ hydrocarbon group or a $C_{1-10}$ alkylsilyl group and may be connected to each other to form rings; and $X^1$, $X^2$, $X^3$ and $x^4$, which may be the same or different from each other, each represents a hydrogen atom, a $C_{1-10}$ hydrocarbon group, a $C_{1-10}$ alkoxy group, a $C_{1-10}$ alkylamino group, a $C_{1-10}$ alkylsilyl group or a halogen atom.

The present invention also relates to a polymerization catalyst comprising, as constituent components, the foregoing organic transition metal compound, an organic aluminum compound, and one or more of compounds capable of cationizing the organic transition metal compound selected from:

a protonic acid represented by the following formula (2):

wherein H represents a proton; $L^1$'s each independently represents a Lewis base; l represents a number of from more than 0 to not more than 2; A represents a boron atom, an aluminum atom or a gallium atom; and $R^{19}$'s each independently represents a $C_{6-20}$ halogen-substituted aryl group;

a Lewis acid represented by the following formula (3):

wherein C represents a carbonium cation or a tropylium cation; A represents a boron atom, an aluminum atom or a gallium atom; and $R^{19}$'s each independently represents a $C_{6-20}$ halogen-substituted aryl group; an ionized ionic compound represented by the following formula (4):

wherein D represents a cation of a metal selected from metals of the groups 1, 2, 8, 9, 10, 11 and 12 of the periodic table; A represents a boron atom, an aluminum atom or a gallium atom; $R^{19}$'s each independently represents a $C_{6-20}$ halogen-substituted aryl group; $L^2$'s each represents a Lewis base or a cyclopentadienyl group; and m represents a number of from not less than 0 to not more than 2; and a Lewis-acid compound represented by the following formula (5):

$$AR^{19}_3 \qquad (5)$$

wherein A represents a boron atom, an aluminum atom or a gallium atom; and $R^{19}$'s each independently represents a $C_{6-20}$ halogen-substituted aryl group.

The present invention further relates to a polymerization catalyst, comprising as, constituent components, the organic transition metal compound and an aluminoxane selected from compounds represented by the following formula (6) or (7):

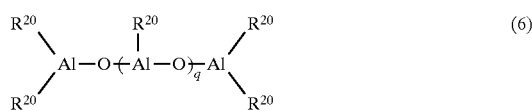

wherein $R^{20}$'s each independently represents a hydrogen atom, a $C_{1-20}$ alkyl group, a $C_{6-20}$ aryl, a $C_{7-20}$ arylalkyl or a $C_{7-20}$ alkylaryl group; and q represents an integer of from 2 to 50.

The present invention still further relates to a process for the preparation of a polyolefin, which comprises the polymerization of an olefin in the presence of the foregoing polymerization catalyst.

BRIEF DESCRIPTION OF THE DRAWINGS

By way of example and to make the description more clear, reference is made to the accompanying drawings in which.

DETAILED DESCRIPTION OF THE INVENTION

Figure 1:
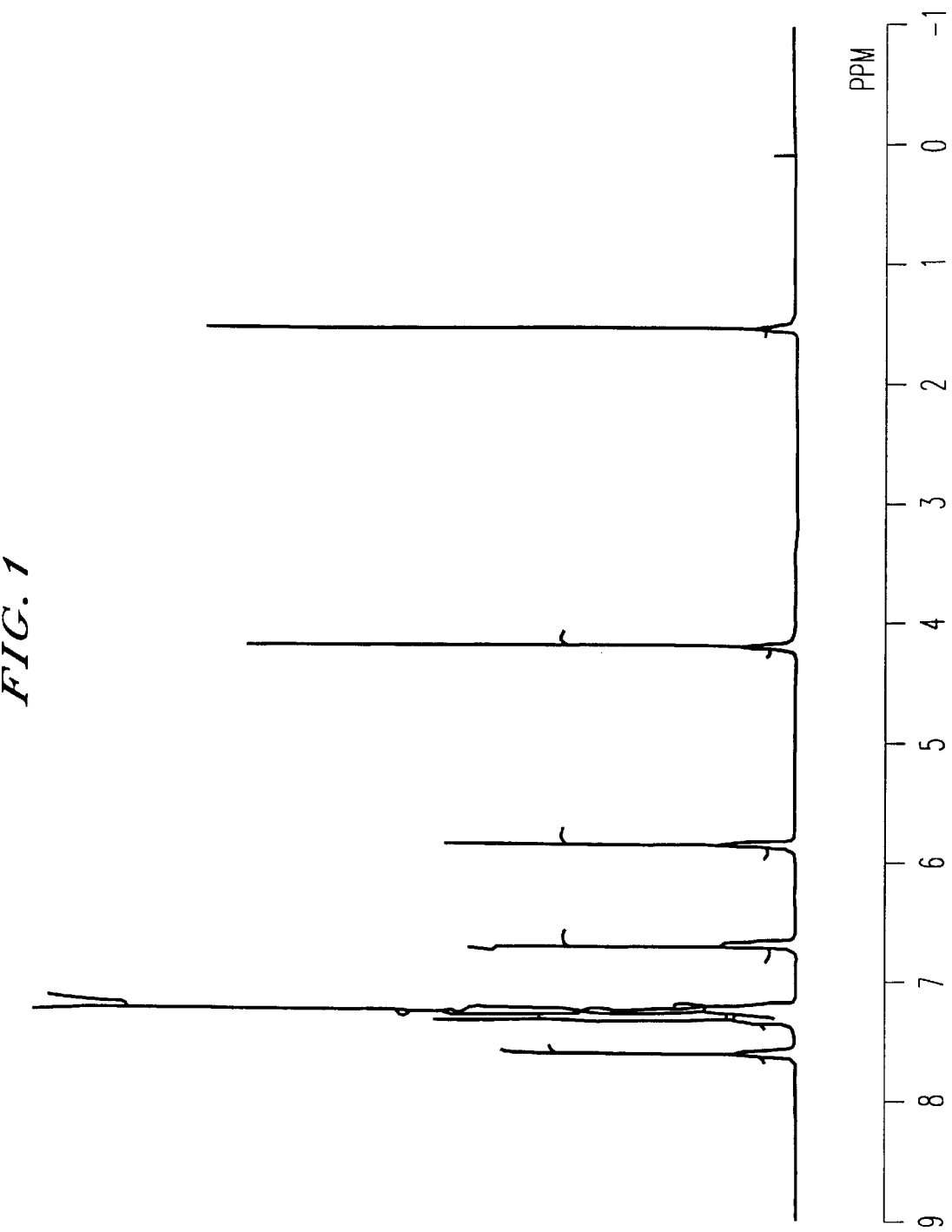
FIG. 1 illustrates $^1$H-NMR spectrum of biindene (dl form) obtained in Example 1.

The present invention will be further described hereinafter. The organic transition metal compound of the present invention is a transition metal compound containing two transition metal atoms per molecule and having a bidentate structure wherein a part of ligands of the atoms are directly conjugated by $\pi$ bond to form a linkage site.

In formula (1), $M^1$ and $M^2$, which may be the same or different from each other, each represents a transition metal atom of the group 4 of the periodic table, selected from the group consisting of a titanium atom, a zirconium atom and a hafnium atom. $R^1$, $R^2$, $R^3$, $R^4$, $R^5$, $R^6$, $R^7$ and $R^8$, which may be the same or different, each represents a hydrogen atom, a $C_{1-10}$ hydrocarbon group or a $C_{1-10}$ alkylsilyl group. $R^1$, $R^2$, $R^3$, $R^4$, $R^5$, $R^6$, $R^7$ and $R^8$ may be connected to each other to form rings. At least one of $R^1$, $R^2$, $R^3$, $R^4$, $R^5$, $R^6$, $R^7$ and $R^8$ is not a hydrogen atom. Specific examples of the group represented by $R^1$, $R^2$, $R^3$, $R^4$, $R^5$, $R^6$, $R^7$ or $R^8$ include a hydrogen atom, an aliphatic hydrocarbon group such as a methyl group, an ethyl group, a propyl group, an isopropyl group, a butyl group and an tert-butyl group, and an alkylsilyl group such as a trimethylsilyl group. $R^1$, $R^2$, $R^3$, $R^4$, $R^5$, $R^6$, $R^7$ and $R^8$ may form a ring with the cyclopentadienyl ring to form an indenyl group, a substituted indenyl group such as a 2-methylindenyl group, a fluorenyl group or a substituted fluorenyl group such as a 2,4-dimethylfluorenyl group and a 2,4-di-tert-butylfluorenyl group. $R^9$, $R^{10}$, $R^{11}$, $R^{12}$, $R^{13}$, $R^{14}$, $R^{15}$, $R^{16}$, $R^{17}$ and $R^{18}$, which are connected to the cyclopentadienyl group, may be the same or different from each other and each represents a hydrogen atom, $C_{1-10}$ hydrocarbon group or a $C_{1-10}$ alkylsilyl group. $R^9$, $R^{10}$, $R^{11}$, $R^{12}$, $R^{13}$, $R^{14}$, $R^{15}$, $R^{16}$, $R^{17}$ and $R^{18}$ may be connected to each other to form rings. Specific examples of the group represented by $R^9$, $R^{10}$, $R^{11}$, $R^{12}$, $R^{13}$, $R^{14}$, $R^{15}$, $R^{16}$, $R^{17}$ or $R^{18}$ include a hydrogen atom, an aliphatic hydrocarbon group such as a methyl group, an ethyl group, a propyl group, an isopropyl group, a butyl group and a tert-butyl group, and an alkylsilyl group such as a trimethylsilyl group. $R^9$, $R^{10}$, $R^{11}$, $R^{12}$, $R^{13}$, $R^{14}$, $R^{15}$, $R^{16}$, $R^{17}$ and $R^{18}$ may form a ring with the cyclopentadienyl ring to form an indenyl group, a substituted indenyl group such as a 2-methylindenyl group, a fluorenyl group or a substituted fluorenyl group such as a 2,4-dimethylfluorenyl group and a 2,4-di-tert-butylfluorenyl group. $X^1$, $X^1$, $X^3$ and $X^4$, which may be the same or different from each other, each represents a hydrogen atom, a $C_{1-10}$ hydrocarbon group such as a methyl group, an ethyl group, a propyl group, an isopropyl group, a butyl group, a tert-butyl group, a phenyl group and a benzyl group, a $C_{1-10}$ alkoxyl group such as a methoxy group, a $C_{1-10}$ alkylamino group such as a dimethylamino group, a $C_{1-10}$ alkylsilyl group such as a trimethylsilyl group or a halogen atom such as a fluorine atom, a chlorine atom, a bromine atom and an iodine atom, preferably a chlorine atom, a methyl group or a benzyl group.

The organic transition metal compound of the present invention represented by formula (1) may have the following isomers depending on the kind of substituents thereon, synthesis method, purification conditions, etc.:

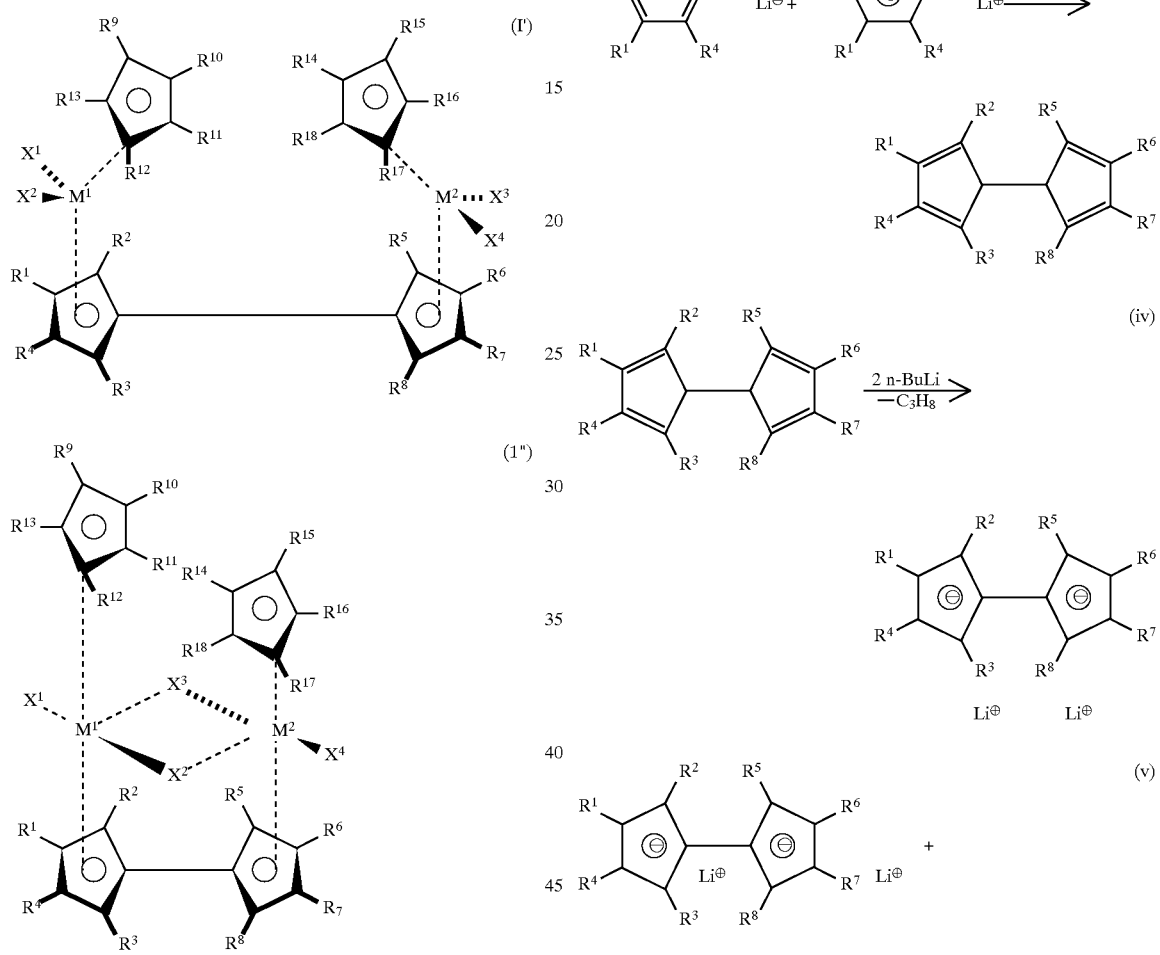

The organic transition metal compound of the present invention represented by formula (1) can be synthesized by, e.g., the following path:

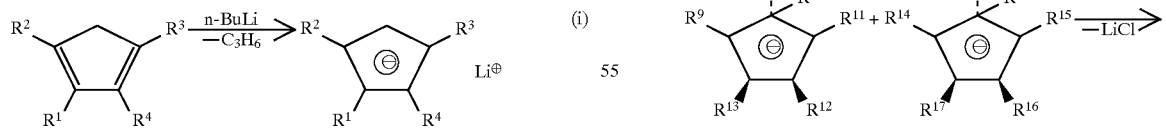

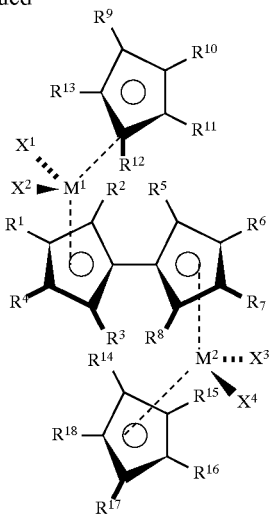

However, the present invention is not limited to the foregoing synthesis path. The coupling reaction of cyclopentadiene, indene, fluorene or a derivative thereof shown in the reaction formula (iii) can be effected by the use of a biindene synthesis method described in *Synthesis*, 203 (1987). In some detail, a substituted cyclopentadiene, indene, fluorene or a derivative thereof is acted with n-butyl lithium to produce a lithium salt which is then acted with anhydrous copper (II) chloride to obtain a bicyclopentadiene derivative. As the method for obtaining a bicyclopentadiene derivative there may be also used a method described in *Helvetica Chemica Acta*, 69, 1644 (1986) which uses iodine coupling. Further, two cyclopentadiene derivatives may be used to synthesize a ligand of the organic transition metal compound represented by formula (1). In accordance with the reaction of bicyclopentadienyl lithium with a transition metal compound shown by the reaction formula (v), the organic transition metal compound represented by formula (1) can be synthesized. Examples of the reaction solvent to be used in this reaction include diethyl ether, tetrahydrofuran, methylene chloride, and toluene. Preferred among these reaction solvents is toluene. The temperature at which the complex synthesis reaction is effected is from −200° C. to 200° C., preferably from −78° C. to 150° C.

The organic transition metal compound of formula (1) thus synthesized can be purified by recrystallization or sublimation. Further, the organic transition metal compound has a bicyclopentadienyl site which is a rigid bidentate ligand having metal-coordinatable sites directly bonded to each other in the complex structure. Therefore, the organic transition metal compound is free from instable factors caused by the structure of a carbon chain linkage site in the foregoing complex and thus is extremely stable and entails no problems of handling.

Examples of the bicyclopentadiene derivative to be used in the synthesis of the organic transition metal compound of the present invention represented by formula (1) include 1,1'-bi(2-methylcyclopentadiene), 1,1'-bi(3-methylcyclopentadiene), 1,1'-bi(2,3-dimethylcyclopentadiene), 1,1'-bi(2,4-dimethylcyclopentadiene), 1,1'-bi(2,5-dimethylcyclopentadiene), 1,1'-bi(3,4-dimethylcyclopentadiene), 1,1'-bi(2,3,4-trimethylcyclopentadiene), 1,1'-bi(2,3,4,5-tetramethylcyclopentadiene), 1,1'-bi(tetramethylsilylpentadiene), 1,1'-biindene, 1,1'-bi(2-methylindene), 1,1'-bi(tetrahydroindene), 1,1'-bifluorene, 1,1'-bi(2,4-dimethylfluorene), 1,1'-bi(2,4-di-tert-butylfluorene), 1,1'-bi(tetrahydrofluorene), 1,1'-bi(octahydrofluorene), 1-cyclopentadienyl-1'-methylcyclopentadiene, 1-cyclopentadienyl-1'-dimethylcyclopentadiene, 1-cylopentadienyl-1'-trimethylcyclo-pentadiene, 1-cyclopentadienyl-1'-tetramethylcyclopentadiene, 1-methylcyclopentadienyl-1'-dimethylcyclopentadiene, 1-methylcyclopentadienyl-1'-trimethylcyclopentadiene, 1-methylcyclopentadienyl-1'-tetramethylcyclopentadiene, 1-dimethylcyclopentadienyl-1'-trimethylcyclopentadiene, 1-dimethylcyclopentadienyl-1'-tetramethylcyclopentadiene, 1-trimethylcyclopentadienyl-1'-tetramethylcyclopentadiene, 1-indenyl-1'-cyclopentadiene, 1-indenyl-1'-methylcyclopentadiene, 1-indenyl-1'-dimethylcyclopentadiene, 1-indenyl-1'-trimethylcyclopentadiene, 1-indenyl-1'-tetramethylcyclopentadiene, 1-fluorenyl-1'-cyclopentadiene, 1-fluorenyl-1'-methylcyclopentadiene, 1-fluorenyl-1'-dimethylcyclopentadiene, 1-fluorenyl-1'-trimethylcyclopentadiene, 1-fluorenyl-1'-tetramethylcyclopentadiene, and 1-indenyl-1'-fluorene. However, the present invention should not be construed as being limited to these compounds.

Specific examples of the transition metal compound to be used in the synthesis of the complex include cyclopentadienylzirconium trichloride, methylcyclopentadienylzirconium trichloride, dimethylcyclopentadienylzirconium trichloride, trimethylcyclopentadienylzirconium trichloride, tetramethylcyclopentadienylzirconium trichloride, pentamethylcyclopentadienylzirconium trichloride, trimethylsilylcyclopentadienylzirconium trichloride, indenylzirconium trichloride, 2-methylindenylzirconium trichloride, tetrahydroindenylzirconium trichloride, fluorenylzirconium trichloride, 2,4-dimethylfluorenyl-zirconium trichloride, 2,4-di-tert-butylzirconium trichloride, tetrahydrofluorenylzirconium trichloride, octahydrofluorenylzirconium trichloride, cyclopentadienylzirconium dimethyl chloride, dimethylcyclopentadienylzirconium dimethyl chloride, trimethylcyclopentadienylzirconium dimethyl chloride, tetramethylcyclopentadienylzirconium dimethyl chloride, pentamethylcyclopentadienylzirconium dimethyl chloride, trimethylsilylcyclopentadienylzirconium dimethyl chloride, indenylzirconium dimethyl chloride, 2-methylindenylzirconium dimethyl chloride, tetrahydroindenylzirconium dimethyl chloride, fluorenylzirconium dimethyl chloride, 2,4-dimethylfluorenylzirconium dimethyl chloride, 2,4-di-tert-butylzirconium trichloride, tetrahydrofluorenylzirconium dimethyl chloride, octahydrofluorenylzirconium dimethyl chloride, cyclopentadienyltitanium trichloride, methylcyclopentadienyltitanium trichloride, dimethylcyclopentadienyltitanium trichloride, trimethylcyclopentadienyltitanium trichloride, tetramethylcyclopentadienyltitanium trichloride, pentamethylcyclopentadienyltitanium trichloride, trimethylsilylcyclopentadienyltitanium trichloride, indenyltitanium trichloride, 2-methylindenyltitanium trichloride, tetrahydroindenyltitanium trichloride, fluorenyltitanium trichloride, 2,4-dimethylfluorenyltitanium trichloride, 2,4-di-tert-butyltitanium trichloride, tetrahydrofluorenyltitanium trichloride, octahydrofluorenyltitanium trichloride, cyclopentadienyltitanium dimethyl chloride, methylcyclopentadienyltitanium dimethyl chloride, dimethylcyclopentadienyltitanium dimethyl chloride, trimethylcyclopentadienyltitanium dimethyl chloride, tetramethylcyclopentadienyltitanium dimethyl chloride, pentamethylcyclopentadienyltitanium dimethyl chloride, trimethylsilylcyclopentadienyltitanium dimethyl chloride, indenyltitanium dimethyl chloride, 2-methylindenyltitanium dimethyl chloride, tetrahydroindenyltitanium dimethyl chloride, fluorenyltitanium dimethyl chloride, 2,4-dimethylfluorenyltitanium dimethyl chloride, 2,4-di-tert-butyltitanium trichloride, tetrahydrofluorenyltitanium dimethyl chloride, octahydrofluorenyltitanium dimethyl chloride, cyclopentadienylhafnium trichloride, methylcyclopentadienylhafnium trichloride, dimethylcyclopentadienylhafnium trichloride, trimethylcyclopentadienylhafnium trichloride, tetramethylcyclopentadienylhafnium trichloride, pentamethylcyclopentadienylhafnium trichloride, trimethylsilylcyclopentadienylhafnium trichloride, indenylhafnium trichloride, 2-methylindenylhafnium trichloride, tetrahydroindenylhafnium trichloride, fluorenylhafnium trichloride, 2,4-dimethylfluorenylhafnium trichloride, 2,4-di-tert-butylhafnium trichloride, tetrahydrofluorenylhafnium trichloride, octahydrofluorenylhafnium trichloride, cyclopentadienylhafnium dimethyl chloride, methylcyclopentadienylhafnium dimethyl chloride, dimethylcyclopentadienylhafnium dimethyl chloride, trimethylcyclopentadienylhafnium dimethyl chloride, tetramethylcyclopentadienylhafnium dimethyl chloride, pentamethylcyclopentadienylhafnium dimethyl chloride, trimethylsilylcyclopentadienylhafnium dimethyl chloride, indenylhafnium dimethyl chloride, 2-methylindenylhafnium dimethyl chloride, tetrahydroindenylhafnium dimethyl chloride, fluorenylhafnium dimethyl chloride, 2,4-dimethylfluorenylhafnium dimethyl chloride, 2,4-di-tert-butylhafnium trichloride, tetrahydrofluorenylhafnium dimethyl chloride, and octahydrofluorenylhafnium dimethyl chloride. The present invention should not construed as being limited to these compounds.

Specific examples of the organic transition metal compound of the present invention represented by formula (1) include (biindenyl)bis(cyclopentadienylzirconium dichloride), (biindenyl)bis(methylcyclopentadienylzirconium dichloride), (biindenyl)bis(1,2-dimethylcyclopentadienylzirconium dichloride), (biindenyl)bis(1,3-dimethylcyclopentadienylzirconium dichloride), (biindenyl)bis(1,2,3-trimethylcyclopentadienylzirconium dichloride), (biindenyl)bis(1,2, 4-trimethylcyclopentadienylzirconium dichloride), (biindenyl)-bis(trimethylsilylcyclopentadienylzirconium dichloride), (biindenyl)bis[di(trimethylsilyl)cyclopentadienylzirconium dichloride], (biindenyl)bis(indenylzirconium dichloride), (biindenyl)bis(2-methylindenylzirconium dichloride), (biindenyl)bis(tetrahydroindenylzirconium dichloride), (biindenyl)bis(fluorenylzirconium dichloride), (biindenyl)bis(2,4-dimethylfluorenylzirconium dichloride), (biindenyl)bis(2,4-di-tert-butylfluorenylzirconium dichloride), (biindenyl)(cyclopentadienyldichlorozirconium)(methylcyclopentadienylzirconium dichloride), (biindenyl)(cyclopentadienyldichlorozirconium)(dimethylcyclopentadienylzirconium dichloride), (biindenyl) (cyclopentadienyldichlorozirconium)(trimethylcyclopentadienylzirconium dichloride), (biindenyl) (cyclopentadienyldichlorozirconium)-(tetramethylcyclopentadienylzirconium dichloride), (biindenyl)(cyclopentadienyldichlorozirconium)(pentamethyl-cyclopentadienylzirconium dichloride), (biindenyl) (methylcyclopentadienyldichlorozirconium)-(dimethylcyclopentadienylzirconium dichloride), (biindenyl)(methylcyclopentadienyldichlorozirconium)-(trimethylcyclopentadienylzirconium dichloride), (biindenyl)(methylcyclopentadienyldichlorozirconium)-(tetramethylcyclopentadienylzirconium dichloride), (biindenyl)(methylcyclopentadienyldichlorozirconium)-(pentamethylcyclopentadienylzirconium dichloride), (biindenyl)(dimethylcyclopentadienyldichlorozirconium)-(trimethylcyclopentadienylzirconium dichloride) (biindenyl)(dimethylcyclopentadienyldichlorozirconium)-(tetramethylcyclopentadienylzirconium dichloride), (biindenyl)(dimethylcyclopentadienyldichlorozirconium)-(pentamethylcyclopentadienylzirconium dichloride), (biindenyl)(trimethylcyclopentadienyldichlorozirconium)-(tetramethylcyclopentadienylzirconium dichloride), (biindenyl)(trimethylcyclopentadienyldichlorozirconium)-(pentamethylcyclopentadienylzirconium dichloride), (biindenyl)(tetramethylcyclopentadienyldichlorozirconium)-(pentamethylcyclopentadienylzirconium dichloride), (biindenyl)(cyclopentadienyldichlorozirconium)-(indenylzirconium dichloride), (biindenyl)(methylcyclopentadienyldichlorozirconium)(indenylzirconium dichloride), (biindenyl)(dimethylcyclopentadienyldichlorozirconium)-(indenylzirconium dichloride), (biindenyl)(trimethylcyclopentadienyldichlorozirconium)(indenylzirconium dichloride), (biindenyl)(tetramethylcyclopentadienyldichlorozirconium)(indenylzirconium dichloride), (biindenyl)-(pentamethylcyclopentadienyldichlorozirconium)-(indenylzirconium dichloride), (biindenyl)(cyclopentadienyldichlorozirconium)(fluorenylzirconium dichloride), (biindenyl)(indenyldichlorozirconium)(fluorenylzirconium dichloride), [bi(dimethylcyclopentadienyl)]bis(cyclopentadienylzirconium dichloride), [bi(dimethylcyclopentadienyl)]bis(methylcyclopentadienylzirconium dichloride), [bi(dimethylcyclopentadienyl)]bis(1,2-dimethylcyclopentadienylzirconium dichloride), [bi(dimethylcyclopentadienyl)]-bis(1,3-dimethylcyclopentadienylzirconium dichloride), [bi(dimethylcyclopentadienyl)]bis(1,2,3-trimethylcyclopentadienylzirconium dichloride), [bi(dimethylcyclopentadienyl)]bis(1,2,4-trimethylcyclopentadienylzirconium dichloride), [bi(dimethylcyclopentadienyl) ]-bis(trimethylsilylcyclopentadienylzirconium dichloride), [bi(dimethylcyclopentadienyl)]bis[di(trimethylsilyl)-cyclopentadienylzirconium dichloride), [bi(dimethylcyclopentadienyl)]bis(indenylzirconium dichloride), [bi(dimethylcyclopentadienyl)]bis(2-methylindenylzirconium dichloride), [bi(dimethylcyclopentadienyl)]bis(tetrahydroindenylzirconium dichloride), [bi(dimethylcyclopentadienyl)]bis(fluorenylzirconium dichloride), [bi(dimethylcyclopentadienyl)]bis(2,4-dimethylfluorenylzirconium dichloride), [bi(dimethylcyclopentadienyl)]bis(2, 4-d-tert-butylfluorenylzirconium dichloride), [bi(dimethylcyclopentadienyl)](cyclopentadienyldichlorozirconium)(methylcyclopentadienylzirconium dichloride), [bi(dimethylcyclopentadienyl)](cyclopentadienyldichlorozirconium)(dimethylcyclopentadienylzirconium dichloride), [bi(dimethylcyclopentadienyl)](cyclopentadienyldichlorozirconium)(trimethylcyclopentadienylzirconium dichloride), [bi(dimethylcyclopentadienyl)](cyclopentadienyldichlorozirconium)(tetramethylcyclopentadienylzirconium dichloride), [bi (dimethylcyclopentadienyl)](cyclopentadienyldichlorozirconium) (pentamethylcyclopentadienylzirconium dichloride), [bi(dimethylcyclopentadienyl)](methylcyclopentadienyldichloro zirconium) (dimethylcyclopentadienylzirconium dichloride), [bi(dimethylcyclopentadienyl)](methylcyclopentadienyldichlorozirconium) (trimethylcyclopentadienylzirconium dichloride), [bi(dimethylcyclopentadienyl)](methylcyclopentadienyldichlorozirconium) (tetramethylcyclopentadienylzirconium dichloride), [bi(dimethylcyclopentadienyl)](methylcyclopentadienyldichlorozirconium) (pentamethylcyclopentadienylzirconium dichloride), [bi(dimethylcyclopentadienyl)](dimethylcyclopentadienyldichlorozirconium) (trimethylcyclopentadienylzirconium dichloride), [bi(dimethylcyclopentadienyl)](dimethylcyclopentadienyldichlorozirconium) (tetramethylcyclopentadienylzirconium dichloride), [bi(dimethylcyclopentadienyl)]-(dimethylcyclopentadienyldichlorozirconium)-(pentamethylcyclopentadienylzirconium dichloride), [bi(dimethylcyclopentadienyl)](trimethylcyclopentadienyldichlorozirconium) (tetramethylcyclopentadienylzirconium dichloride), [bi(dimethylcyclopentadienyl)]-(trimethylcyclopentadienyldichlorozirconium)-(pentamethylcyclopentadienylzirconium dichloride), [bi(dimethylcyclopentadienyl)](tetramethylcyclopentadienyldichlorozirconium) (pentamethylcyclopentadienylzirconium dichloride), [bi(dimethylcyclopentadienyl)](cyclopentadienyldichlorozirconium) (indenylzirconium dichloride), [bi(dimethylcyclopentadienyl)](methylcyclopentadienyldichlorozirconium) (indenylzirconium dichloride), [bi(dimethylcyclopentadienyl)](dimethylcyclopentadienyldichlorozirconium) (indenylzirconium dichloride), [bi(dimethylcyclopentadienyl)](trimethylcyclopentadienyldichlorozirconium) (indenylzirconium dichloride), [bi(dimethylcyclopentadienyl)](tetramethylcyclopentadienyldichlorozirconium) (indenylzirconium dichloride), [bi(dimethylcyclopentadienyl)](pentamethylcyclopentadienyldichlorozirconium) (indenylzirconium dichloride), [bi(dimethylcyclopentadienyl)](cyclopentadienyldichlorozirconium) (fluorenylzirconium dichloride), [bi(dimethylcyclopentadienyl)](indenyldichlorozirconium)(fluorenylzirconium dichloride), [bi(trimethylcyclopentadienyl)]bis(cyclopentadienylzirconium dichloride), [bi(trimethylcyclopentadienyl)]-bis(methylcyclopentadienylzirconium dichloride), [bi(trimethylcyclopentadienyl)]bis(1,2-dimethylcyclopentadienylzirconium dichloride), [bi(trimethylcyclopentadienyl)]-bis(1,3-dimethylcyclopentadienylzirconium dichloride), [bi(trimethylcyclopentadienyl)]bis(1,2,3-trimethylcyclopentadienylzirconium dichloride), [bi(trimethylcyclopentadienyl)]bis(1,2,4-trimethylcyclopentadienylzirconium dichloride), [bi(trimethylcyclo-pentadienyl)]bis(trimethylsilylcyclopentadienylzirconium dichloride), [bi(trimethylcyclopentadienyl)]bis[di(trimethyl-silyl) cyclopentadienylzirconium dichloride], [bi(trimethylcyclopentadienyl)]bis(indenylzirconium dichloride), [bi(trimethylcyclopentadienyl)]bis(2-methylindenylzirconium dichloride), [bi(trimethylcyclopentadienyl)]bis(tetrahydroindenylzirconium dichloride), [bi(trimethylcyclopentadienyl)]bis(fluorenylzirconium dichloride), [bi(trimethylcyclopentadienyl)]bis(2,4-dimethylfluorenylzirconium dichloride), [bi(trimethylcyclopentadienyl)]bis(2,4-di-tertbutylfluorenylzirconium dichloride), [bi(trimethylcyclopentadienyl)](cyclopentadienyldichlorozirconium)-(methylcyclopentadienylzirconium dichloride), [bi(trimethylcyclopentadienyl)](cyclopentadienyldichlorozirconium) (dimethylcyclopentadienylzirconium dichloride), [bi(trimethylcyclopentadienyl)](cyclopentadienyldichlorozirconium) (trimethylcyclopentadienylzirconium dichloride), [bi(trimethylcyclopentadienyl)]-(cyclopentadienyldichlorozirconium) (tetramethylcyclopentadienylzirconium dichloride), [bi(trimethylcyclopentadienyl)](cyclopentadienyldichlorozirconium)-(pentamethylcyclopentadienylzirconium dichloride), [bi(trimethylcyclopentadienyl)](methylcyclopentadienyldichlorozirconium) (dimethylcyclopentadienylzirconium dichloride), [bi(trimethylcyclopentadienyl)]-(methylcyclopentadienyldichlorozirconium)-(trimethylcyclopentadienylzirconium dichloride), [bi(trimethylcyclopentadienyl)](methylcyclopentadienyldichlorozirconium) (tetramethylcyclopentadienylzirconium dichloride), [bi(trimethylcyclopentadienyl)](methylcyclopentadienyldichlorozirconium) (pentamethylcyclopentadienylzirconium dichloride), [bi(trimethylcyclopentadienyl)](dimethylcyclopentadienyldichlorozirconium)-(trimethylcyclopentadienylzirconium dichloride), [bi(trimethylcyclopentadienyl)](dimethylcyclopentadienyldichlorozirconium) (tetramethylcyclopentadienylzirconium dichloride), [bi(trimethylcyclopentadienyl)](dimethylcyclopentadienyldichlorozirconium) (pentamethylcyclopentadienylzirconium dichloride), [bi(trimethylcyclopentadienyl)]-(trimethylcyclopentadienyldichlorozirconium)-(tetramethylcyclopentadienylzirconium dichloride), [bi(trimethylcyclopentadienyl)](trimethylcyclopentadienyldichlorozirconium) (pentamethylcyclopentadienylzirconium dichloride), [bi(trimethylcyclopentadienyl)](tetramethylcyclopentadienyldichlorozirconium) (pentamethylcyclopenta-dienylzirconium dichloride), [bi(trimethylcyclopentadienyl)]-(cyclopentadienyldichlorozirconium) (indenylzirconium dichloride), [bi(trimethylcyclopentadienyl)](methylcyclopentadienyldichlorozirconium) (indenylzirconium dichloride), [bi(trimethylcyclopentadienyl)](dimethylcyclopentadienyldichlorozirconium) (indenylzirconium dichloride), [bi(trimethylcyclopentadienyl)]

(trimethylcyclopentadienyldichlorozirconium)(indenylzirconium dichloride), [bi(trimethylcyclopentadienyl)](tetramethylcyclopentadienyldichlorozirconium)(indenylzirconium dichloride), [bi(trimethylcyclopentadienyl)](pentamethylcyclopentadienyldichlorozirconium)(indenylzirconium dichloride), [bi(trimethylcyclopentadienyl)](cyclopentadienyldichlorozirconium)(fluorenylzirconium dichloride), [bi(trimethylcyclopentadienyl)](indenyldichlorozirconium)-(fluorenylzirconium dichloride), [bi(trimethylcyclopentadienyl)]bis(cyclopentadienylzirconium dichloride), [bi(tetramethylcyclopentadienyl)]bis(methylcyclopentadienylzirconium dichloride), [bi(tetramethylcyclopenta-dienyl)]bis(1,2-dimethylcyclopentadienylzirconium dichloride), [bi(tetramethylcyclopentadienyl)]bis(1,3-dimethylcyclopentadienylzirconium dichloride), [bi(tetramethylcyclopentadienyl)]bis(1,2,3-trimethylcyclopentadienylzirconium dichloride), [bi(tetramethyl-cyclopentadienyl)]bis(1,2,4-trimethylcyclopentadienylzirconium dichloride), [bi(tetramethylcyclopentadienyl)]-bis(trimethylsilylcyclopentadienylzirconium dichloride), [bi(tetramethylcyclopentadienyl)]bis[di(trimethylsilyl)-cyclopentadienylzirconium dichloride), [bi(tetramethylcyclopentadienyl)]bis(indenylzirconium dichloride), [bi(tetramethylcyclopentadienyl)]bis(2-methylindenylzirconium dichloride), [bi(tetramethylcyclopentadienyl)]bis-(tetrahydroindenylzirconium dichloride), [bi(tetramethylcyclopentadienyl)]bis(fluorenylzirconium dichloride), [bi(tetramethylcyclopentadienyl)]bis(2,4-dimethylfluorenylzirconium dichloride), [bi(tetramethyl-cyclopentadienyl)]bis(2,4-di-tert-butylfluorenylzirconium dichloride), [bi(tetramethylcyclopentadienyl)](cyclopentadienyldichlorozirconium)(methylcyclopentadienylzirconium dichloride), [bi(tetramethylcyclopentadienyl)]-(cyclopentadienyldichlorozirconium)(dimethylcyclopentadienylzirconium dichloride), [bi(tetramethylcyclopentadienyl)](cyclopentadienyldichlorozirconium)(trimethylcyclopentadienylzirconium dichloride), [bi(tetramethylcyclopentadienyl)](cyclopentadienyldichlorozirconium)-(tetramethylcyclopentadienylzirconium dichloride), [bi(tetramethylcyclopentadienyl)](cyclopentadienyldichlorozirconium)(pentamethylcyclopentadienylzirconium dichloride), [bi(tetramethylcyclopentadienyl)](methylcyclopentadienyl-dichlorozirconium)(dimethylcyclopentadienylzirconium dichloride), [bi(tetramethylcyclopentadienyl)](methylcyclopentadienyldichlorozirconium)(trimethylcyclopentadienyl-zirconium dichloride), [bi(tetramethylcyclopentadienyl)]-(methylcyclopentadienyldichlorozirconium)(tetramethylcyclopentadienylzirconium dichloride), [bi(tetramethylcyclopenta-dienyl)](methylcyclopentadienyldichlorozirconium)-(pentamethylcyclopentadienylzirconium dichloride), [bi(tetramethylcyclopentadienyl)](dimethylcyclopentadienyl-dichlorozirconium)(trimethylcyclopentadienyldichlorozirconium dichloride), [bi(tetramethylcyclopentadienyl)](dimethylcyclo-pentadienyldichlorozirconium)(tetramethylcyclopentadienylzirconium dichloride), [bi(tetramethylcyclopentadienyl)]-(dimethylcyclopentadienyldichlorozirconium)(pentamethylcyclopentadienylzirconium dichloride), [bi(tetramethylcyclopentadienyl)](trimethylcyclopentadienyldichlorozirconium)-(tetramethylcyclopentadienylzirconium dichloride), [bi(tetramethylcyclopentadienyl)](trimethylcyclopentadienyldichlorozirconium)(pentamethylcyclopentadienylzirconium dichloride), [bi(tetramethylcyclopentadienyl)](tetramethylcyclopentadienyldichlorozirconium)(pentamethylcyclopentadienylzirconium dichloride), [bi(tetramethylcyclopentadienyl)](cyclopentadienyldichlorozirconium)(indenylzirconium dichloride), [bi(tetramethylcyclopentadienyl)](methylcyclopentadienyldichlorozirconium)(indenylzirconium dichloride), [bi(tetramethylcyclopentadienyl)](dimethylcyclopentadienyldichlorozirconium)(indenylzirconium dichloride), [bi(tetramethylcyclopentadienyl)](trimethylcyclopentadienyldichlorozirconium)(indenylzirconium dichloride), [bi(tetramethylcyclopentadienyl)](tetramethylcyclopentadienyldichlorozirconium)(indenylzirconium dichloride), [bi(tetramethylcyclopentadienyl)](pentamethylcyclopentadienyldichlorozirconium)(indenylzirconium dichloride), [bi(tetramethylcyclopentadienyl)](cyclopentadienyldichlorozirconium)(fluorenylzirconium dichloride), [bi(tetramethylcyclopentadienyl)](indenyldichlorozirconium)-(fluorenylzirconium dichloride), [bi(pentamethylcyclopentadienyl)]bis(cyclopentadienylzirconium dichloride), [bi(pentamethylcyclopentadienyl)]bis(methylcyclopentadienylzirconium dichloride), [bi(pentamethylcyclopentadienyl)]-bis(1,2-dimethylcyclopentadienylzirconium dichloride), [bi(pentamethylcyclopentadienyl)]bis(1,3-dimethylcyclopentadienylzirconium dichloride), [bi(pentamethylcyclopentadienyl)]bis(1,2,3-trimethylcyclopentadienylzirconium dichloride), [bi(pentamethylcyclopentadienyl)]bis(1,2,4-trimethylcyclopentadienylzirconium dichloride), [bi(pentamethylcyclopentadienyl)]bis(trimethylsilylcyclopentadienylzirconium dichloride), [bi(pentamethylcyclo-pentadienyl)]bis[di(trimethylsilyl)cyclopentadienylzirconium dichloride), [bi(pentamethylcyclopentadienyl)]bis(indenylzirconium dichloride), [bi(pentamethylcyclopentadienyl)]-bis(2-methylindenylzirconium dichloride), [bi(pentamethylcyclopentadienyl)]bis(tetrahydroindenylzirconium dichloride), [bi(pentamethylcyclopentadienyl)]bis(fluorenylzirconium dichloride), [bi(pentamethylcyclopentadienyl)]bis(2,4-dimethylfluorenylzirconium dichloride), [bi(pentamethylcyclopentadienyl)]bis(2,4-di-tert-butylfluorenylzirconium dichloride), [bi(pentamethylcyclopentadienyl)](cyclopentadienyldichlorozirconium)(methylcyclopentadienylzirconium dichloride), [bi(pentamethylcyclopentadienyl)](cyclopentadienyldichlorozirconium)(dimethylcyclopentadienylzirconium dichloride), [bi(pentamethylcyclopentadienyl)](cyclopentadienyldichlorozirconium)

(trimethylcyclopentadienylzirconium dichloride), [bi(pentamethylcyclopentadienyl)](cyclopentadienyldichlorozirconium)(tetramethylcyclopentadienylzirconium dichloride), [bi(pentamethylcyclopentadienyl)](cyclopentadienyldichlorozirconium)(pentamethylcyclopentadienylzirconium dichloride), [bi(pentamethylcyclopentadienyl)](methylcyclopentadienyldichlorozirconium)(dimethylcyclopentadienylzirconium dichloride), [bi(pentamethylcyclopentadienyl)](methylcyclopentadienyldichlorozirconium)(trimethylcyclopentadienylzirconium dichloride), [bi(pentamethylcyclopentadienyl)](methylcyclopentadienyldichlorozirconium)-(tetramethylcyclopentadienylzirconium dichloride), [bi(pentamethylcyclopentadienyl)](methylcyclopentadienyldichlorozirconium)(pentamethylcyclopentadienylzirconium dichloride), [bi(pentamethylcyclopentadienyl)]-(dimethylcyclopentadienyldichlorozirconium)-(trimethylcyclopentadienylzirconium dichloride), [bi(pentamethylcyclopentadienyl)](dimethylcyclopentadienyldichlorozirconium)(tetramethylcyclopentadienylzirconium dichloride), [bi(pentamethylcyclopentadienyl)](dimethylcyclopentadienyldichlorozirconium)(pentamethylcyclopentadienylzirconium dichloride), [bi(pentamethylcyclopentadienyl)](trimethylcyclopentadienyldichlorozirconium)-(tetramethylcyclopentadienylzirconium dichloride), [bi(pentamethylcyclopentadienyl)](trimethylcyclopentadienyl-dichlorozirconium)(pentamethylcyclopentadienylzirconium dichloride), [bi(pentamethylcyclopentadienyl)]-(tetramethylcyclopentadienyldichlorozirconium)-(pentamethylcyclopentadienylzirconium dichloride), [bi(pentamethylcyclopentadienyl)](cyclopentadienyldichlorozirconium)-(indenylzirconium dichloride), [bi(pentamethylcyclopentadienyl)](methylcyclopentadienyldichlorozirconium)(indenylzirconium dichloride), [bi(pentamethylcyclopentadienyl)](dimethylcyclopentadienyldichlorozirconium)(indenylzirconium dichloride), [bi(pentamethylcyclopentadienyl)](trimethylcyclopentadienyldichlorozirconium)(indenylzirconium dichloride), [bi(pentamethylcyclopentadienyl)](tetramethylcyclopentadienyldichlorozirconium)(indenylzirconium dichloride), [bi(pentamethylcyclopentadienyl)](pentamethylcyclopentadienyldichlorozirconium)(indenylzirconium dichloride), [bi(pentamethylcyclopentadienyl)]-(cyclopentadienyldichlorozirconium) (fluorenylzirconium dichloride), [bi(pentamethylcyclopentadienyl)]-(indenyldichlorozirconium) (fluorenylzirconium dichloride), (bifluorenyl)bis(cyclopentadienylzirconium dichloride), (bifluorenyl)bis(methylcyclopentadienylzirconium dichloride), (bifluorenyl)bis(1,2-dimethylcyclopentadienylzirconium dichloride), (bifluorenyl)bis(1,3-dimethylcyclopentadienylzirconium dichloride), (bifluorenyl)bis(1,2,3-trimethylcyclopentadienylzirconium dichloride), (bifluorenyl)bis(1,2,4-trimethylcyclopentadienylzirconium dichloride), (bifluorenyl)bis(trimethylsilylcyclopentadienylzirconium dichloride), (bifluorenyl)bis[di(trimethylsilyl)cyclopentadienylzirconium dichloride], (bifluorenyl)bis(2-methylindenylzirconium dichloride), (bifluorenyl)bis-(tetrahydroindenylzirconium dichloride), (bifluorenyl)bis(fluorenylzirconium dichloride), (bifluorenyl)bis(2,4-dimethylfluorenylzirconium dichloride), (bifluorenyl)bis(2,4-di-tert-butylfluorenylzirconium dichloride), (bifluorenyl)(cyclopentadienyldichlorozirconium)(methylcyclopentadienylzirconium dichloride), (bifluorenyl)(cyclopentadienyldichlorozirconium)-(dimethylcyclopentadienylzirconium dichloride), (bifluorenyl)(cyclopentadienyldichlorozirconium)-(trimethylcyclopentadienylzirconium dichloride), (bifluorenyl)(cyclopentadienyldichlorozirconium)(tetramethylcyclopentadienylzirconium dichloride), (bifluorenyl) (cyclo-pentadienyldichlorozirconium)(pentamethylcyclopentadienylzirconium dichloride), (bifluorenyl)(methylcyclopentadienyldichlorozirconium)(dimethylcyclopentadienylzirconium dichloride), (bifluorenyl)(methylcyclopentadienyldichlorozirconium)(trimethylcyclopentadienylzirconium dichloride), (bifluorenyl)(methylcyclopentadienyldichlorozirconium)-(tetramethylcyclopentadienylzirconium dichloride), (bifluorenyl)(methylcyclopentadienyldichlorozirconium)-(pentamethylcyclopentadienylzirconium dichloride), (bifluorenyl)(dimethylcyclopentadienyldichlorozirconium)-(trimethylcyclopentadienylzirconium dichloride), (bifluorenyl)(dimethylcyclopentadienyldichlorozirconium)-(tetramethylcyclopentadienylzirconium dichloride), (bifluorenyl)(dimethylcyclopentadienyldichlorozirconium)(pentamethylcyclopentadienylzirconium dichloride), (bifluorenyl)(trimethylcyclopentadienyldichlorozirconium)-(tetramethylcyclopentadienylzirconium dichloride), (bifluorenyl)(trimethylcyclopentadienyldichlorozirconium)(pentamethylcyclopentadienylzirconium dichloride), (bifluorenyl)(tetramethylcyclopentadienyldichlorozirconium)-(pentamethylcyclopentadienylzirconium dichloride), (bifluorenyl)(cyclopentadienyldichlorozirconium)-(indenylzirconium dichloride), (bifluorenyl)(methylcyclopentadienyldichlorozirconium)(indenylzirconium dichloride), (bifluorenyl)(dimethylcyclopentadienyldichlorozirconium)-(indenylzirconium dichloride), (bifluorenyl)(trimethylcyclopentadienyldichlorozirconium)(indenylzirconium dichloride), (bifluorenyl)(teramethylcyclopentadienyldichlorozirconium)-(indenylzirconium dichloride), (bifluorenyl)(pentamethylcyclopentadienyldichlorozirconium)(indenylzirconium dichloride), (bifluorenyl)(cyclopentadienyldichlorozirconium) (fluorenylzirconium dichloride), and (bifluorenyl)(indenyldichlorozirconium)(fluorenylzirconium dichloride). In these organic transition metal compounds represented by formula (1), the two transition metal atoms $M^1$ and $M^2$ may be titanium atoms or hafnium atoms instead of the zirconium atoms. Alternatively, $M^1$ may be a titanium atom instead of the zirconium atom while $M^2$ is still the zirconium atom, or vice versa. Further, $M^1$ and $M^2$ may respectively be a titanium atom and a hafnium atom instead of the zirconium atoms, or vice versa. Moreover, $M^2$ is a hafnium atom while $M^1$ is the zirconium atom, or vice versa. Still further, the ligand of the transition metal atom may be a hydrogen atom, a methyl group or a benzyl group instead of the chlorine atom.

The present invention also relates to a polymerization catalyst comprising the foregoing organic transition metal compound as a main catalyst and a process for the preparation of a polyolefin, which comprises the polymerization of an olefin in the presence of the polymerization catalyst. The components to be used as the other constituents of the polymerization catalyst, i.e., a protonic acid represented by formula (2), a Lewis acid represented by formula (3), an ionized ionic compound represented by formula (4) and a Lewis-acidic-compound represented by formula (5) are compounds capable of cationizing the foregoing organic transition metal compound, and they exert a weak coordination to or interaction with the cationic compound thus produced but provide non-reactive paired anion.

Specific examples of the protonic acid represented by formula (2) include diethyloxoniumtetrakis(pentafluorophenyl)borate, dimethyloxoniumtetrakis(pentafluorophenyl)-borate, tetramethyleneoxoniumtetrakis(pentafluorophenyl)-borate, hydroniumtetrakis(pentafluorophenyl)borate, N,N-dimethylanilinumtetrakis(pentafluorophenyl)borate, tri-n-butylammoniumtetrakis(pentafluorophenyl)borate, diethyloxoniumtetrakis(pentafluorophenyl)aluminate, dimethyloxoniumtetrakis(pentafluorophenyl)aluminate, tetramethyleneoxoniumtetrakis(pentafluorophenyl)aluminate, hydroniumtetrakis(pentafluorophenyl)aluminate, N,N-dimethylaniliniumtetrakis(pentafluorophenyl)aluminate, and tri-n-butylammoniumtetrakis(pentafluorophenyl)aluminate. However, the present invention should not be construed as being limited to these compounds.

Specific examples of the Lewis acid represented by formula (3) include trityltetrakis(pentafluorophenyl)borate, trityltetrakis(pentafluorophenyl)aluminate, tropyliumterakis(pentafluorophenyl)borate, and tropyliumtetrakis(pentafluorophenyl)aluminate. However, the present invention should not be construed as being limited to these compounds.

Specific examples of the ionized ionic compound represented by formula (4) include lithium salts such as lithiumtetrakis(pentafluorophenyl)borate and lithiumtetrakis(pentafluorophenyl)aluminate, ether complex thereof, ferrocenium salts such as ferroceniumtetrakis(pentafluorophenyl)borate and ferroceniumtetrakis(pentafluorophenyl)aluminate, and silver salts such as silvertetrakis(pentafluorophenyl)borate and silvertetrakis(pentafluorophenyl)aluminate. However, the present invention should not be construed as being limited to these compounds.

Specific examples of the Lewis-acidic-compound represented by formula (5) include tris(pentafluorophenyl)boran, tris(2,3,5,6-tetrafluorophenyl)boran, tris(2,3,4,5-tetraphenylphenyl)boran, tris(3,4,5-trifluorophenyl)boran, phenylbis(perfluorophenyl)boran, and tris(3,4,5-trifluorophenyl)aluminum. However, the present invention should not be construed as being limited to these compounds.

As the organic aluminum compound to be used in combination with the protonic acid, the Lewis acid, the ionized ionic compound or the Lewis-acid compound there may be used a compound represented by the following formula (8):

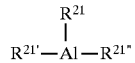 (8)

wherein $R^{21}$, $R^{21'}$ and $R^{21''}$, which may be the same or different from each other, each represents a hydrogen atom, a halogen atom, an amido group, an alkoxide group or a hydrocarbon group, with the proviso that at least one of $R^{21}R^{21'}$ and $R^{21''}$ is a hydrocarbon group.

Preferred examples of the group represented by $R^{21}$, $R^{21'}$ and $R^{21''}$ include a hydrogen atom, a halogen atom, a $C_{1-10}$ amido group, a $C_{1-10}$ alkoxide group and a $C_{1-10}$ hydrocarbon group.

Specific examples of the compound include trimethylaluminum, triethylaluminum, triisobutylaluminum, dimethylaluminum chloride, and diethylaluminum chloride.

The polymerization catalyst can be prepared by combining the organic transition metal compound with an aluminoxane of formula (6) or (7) as follows:

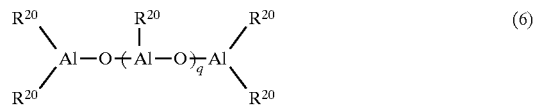 (6)

or

 (7)

wherein $R^{20}$'s each independently represents hydrogen, $C_{1-20}$ alkyl, $C_{7-20}$ arylalkyl or a $C_{1-20}$ alkylaryl; and q represents an integer of from 2 to 50.

The process for the preparation of a catalyst from the foregoing compounds and the organic transition metal compound is not specifically limited. For example, the catalyst may be prepared by mixing these two components with the use of a solvent inert to these components or a monomer to be polymerized as a solvent. The order of the reaction of these components is not specifically limited. The reaction time and temperature are not specifically limited.

The ratio of the organic transition metal compound to the organic aluminum compound during the preparation of the catalyst is not specifically limited, but the molar ratio of the organic transition metal compound to the metal atom in the organic aluminum compound is preferably from 100:1 to 1:100,000, particularly from 1:1 to 1:10,000.

The ratio of the organic transition metal compound to the protonic acid, the Lewis acid, the ionized ionic compound and/or the Lewis-acid compound is not specifically limited, but the molar ratio of the organic transition metal compound to these compounds (the protonic acid, the Lewis acid, the ionized ionic compound and/or the Lewis-acid compound) is preferably from 10:1 to 1:1,000, particularly from 3:1 to 1:100.

The present invention further relates to a polymerization catalyst comprising the foregoing organic transition metal compound and an aluminoxane as constituent components and a process for the preparation of a polyolefin, which comprises the polymerization of an olefin in the presence of the polymerization catalyst. The aluminoxane employable herein is a compound having an aluminum-oxygen bond represented by formula (6) or (7). In these formulae (6) and (7), $R^{20}$'s, which may be the same or different from each other, each represents a hydrogen atom, a $C_{1-20}$ alkyl group, a $C_{6-20}$ aryl group, a $C_{7-20}$ arylalkyl group or a $C_{7-20}$ alkylaryl group. Specific examples of these groups include a methyl group, an ethyl group, a propyl group, a butyl group, a hexyl group, a phenyl group, a tolyl group, and a cyclohexyl group. The suffix q represents an integer of from 2 to 50.

The process for the preparation of a catalyst from the aluminoxane and the organic transition metal compound is not specifically limited. For example, the catalyst may be prepared by mixing these two compounds with the use of a solvent inert to these compounds or a monomer to be polymerized as a solvent. The temperature for this treatment and time are not specifically limited.

The ratio of the organic transition metal compound to the aluminoxane during the preparation of the catalyst is not specifically limited, but the molar ratio of the organic transition metal compound to the metal atom in the aluminoxane is preferably from 100:1 to 1:1,000,000, particularly from 1:1 to 1:100,000.

The polymerization according to the present invention may be an ordinary polymerization method such as slurry polymerization, gas phase polymerization, high pressure polymerization, solution polymerization and bulk polymerization.

When the organic transition metal compound is used as a catalyst component in the polymerization process of the present invention, two or more of them may be used in combination.

As the solvent, if used in the polymerization process of the present invention, there may be used any of generally used organic solvent. Specific examples of such an organic solvent include benzene, toluene, xylene, pentane, hexane, heptane, and methylene chloride. An olefin such as propylene, butene-1, octene-1 and hexene-1 may be used as a solvent by itself.

Examples of the olefin to be polymerized in the present invention include an α-olefin such as ethylene, propylene, butene-1, 4-methylpentene-1, hexene-1, octene-1 and styrene, a conjugated or non-conjugated diene such as α-olefin, butadiene, 1,4-hexadiene, 5-ethylidene-2-norbornene, dicyclopentadiene, 4-methyl-1,4-hexadiene and 7-methyl-1,6-octadiene, and a cyclic olefin such as cyclobutene. Further, two or more olefins may be used in admixture, such as ethylene, propylene and styrene; ethylene, hexene-1 and styrene; and ethylene, propylene and ethylidiene norbornene.

In the preparation of a polyolefin according to the polymerization process of the present invention, polymerization conditions such as the polymerization temperature, the polymerization time, the polymerization pressure and the monomer concentration are not specifically limited, but the polymerization temperature is preferably from −100° C. to 300° C. The polymerization time is preferably from 20 seconds to 20 hours, and the polymerization pressure is preferably from normal pressure to 3,000 kg/cm$^2$G. During the polymerization process, hydrogen or the like may be used to control the molecular weight of the product. The polymerization may be carried out in a batchwise, semi-continuous or continuous manner. Alternatively, the polymerization process may be carried out in two or more stages with varied conditions. Further, the polyolefin obtained by the polymerization process can be recovered from the polymerization apparatus by any conventionally known method, and then dried to obtain the desired polyolefin.

The present invention will be further described in the following examples, but the present invention should not be construed as being limited thereto.

All the reactions were carried out in an atmosphere of inert gas. The solvents used in these reactions had all been previously subjected to purification, drying or deoxidation by a known method. The identification of the organic metal compounds was accomplished by the use of a $^1$H-NMR measuring apparatus (Type GPX-400 NMR measuring apparatus, available from Jeol Ltd.).

EXAMPLE 1

(Synthesis of biindene)

36 m of a 1.64 mol/l hexane solution of n-BuLi was slowly added dropwise to 6.24 g (53.7 mmol) of indene dissolved in 100m of diethyl ether which had been cooled to a temperature of −78° C. in nitrogen stream. The mixture was stirred at a temperature of −78° C. for 30 minutes, and then at a temperature of −30° C. for 30 minutes. To the resulting suspension was then added slowly 7.41 g (55 mmol) of anhydrous copper (II) chloride suspended in 100 m of diethyl ether which had been cooled to a temperature of −30° C. The mixture was then stirred at a temperature of −30° C. for 30 minutes. To the reaction solution was then added water to stop the reaction. The reaction solution was then extracted with diethyl ether. The extract was then dried over anhydrous magnesium sulfate. To the extract thus dried was then added activated carbon and thereafter the extract was filtered and evaporated to remove the solvent therefrom to obtain a reaction mixture in the form of a light brown solid. The reaction mixture thus obtained was then cooled with chilled methanol to obtain a colorless solid (2.81 g).

$^1$H-NMR spectrum (CDCl$_3$) of the solid thus obtained was as follows:

| dl form: | δ = 4.20 | (s, Ind-H) |
|---|---|---|
| | 5.86 | (d, Cp) |
| | 6.71 | (d, Cp) |
| | 7.2–7.6 | (m, aromatic-H) |
| meso form: | δ = 4.16 | (s, Ind-H) |
| | 6.35 | (d, Cp) |
| | 6.75 | (d, Cp) |
| | 6.9–7.2 | (m, aromatic-H). |

The measured melting point of the solid (dl form) was 98° C. Biindene has a melting point of 99° C. (dl form) according to the literature. Thus, the solid thus obtained was identified as biindene.

Figure 2:
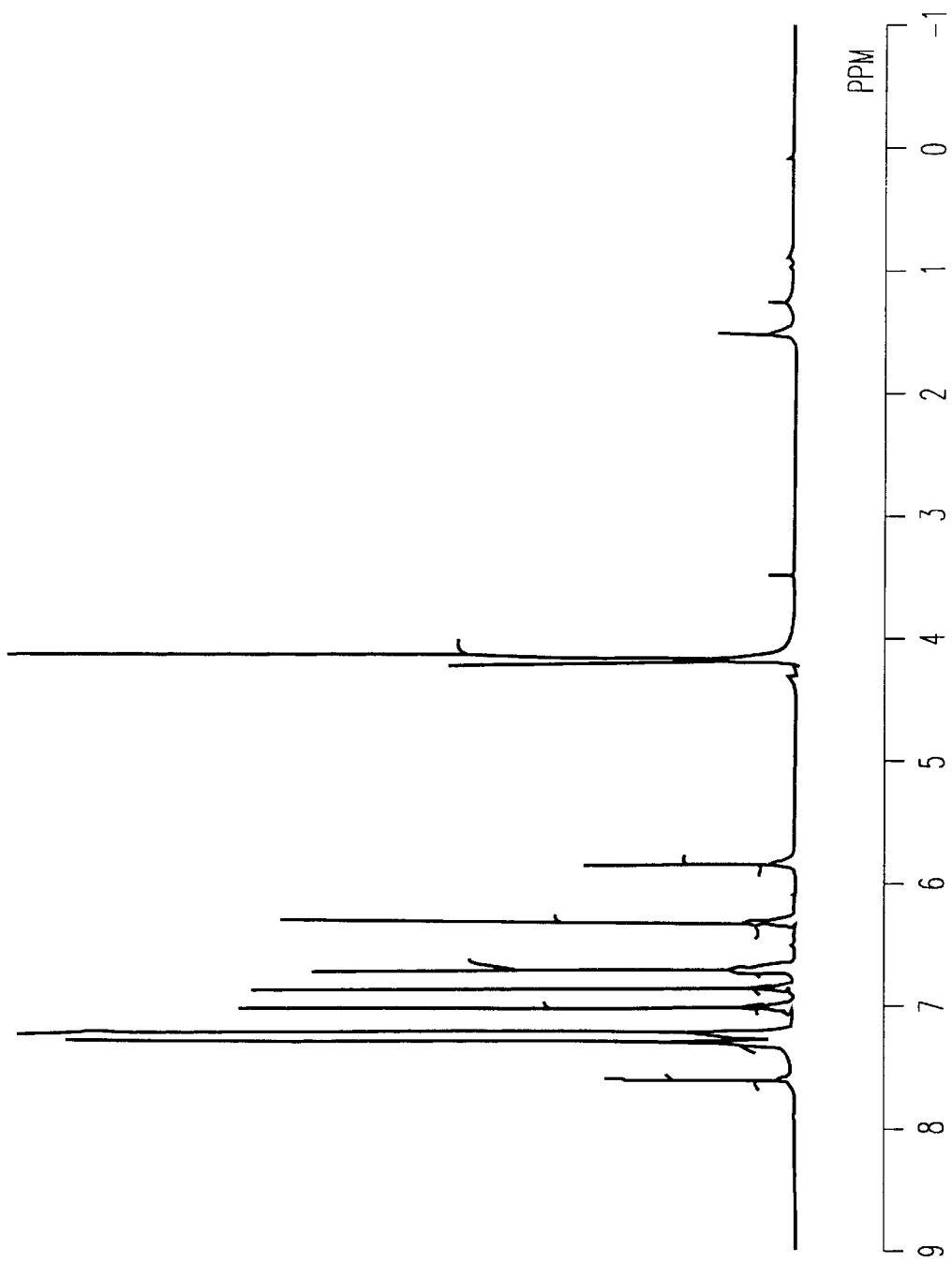
FIG. 2 illustrates $^1$H-NMR spectrum of biindene (mixture of meso form and dl form) obtained in Example 1.

$^1$H-NMR spectrum of this compound is shown in FIGS. 1 and 2.

EXAMPLE 2

(Synthesis of (biindenyl)bis (cyclopentadienylzirconium dichloride)

3 ml of a 1.64 mol/l hexane solution of n-BuLi was slowly added dropwise to 0.51 g (2.2 mmol) of biindene dissolved in 50 ml of hexane which had been cooled to a temperature of 0° C. in nitrogen stream. The mixture was stirred at a temperature of 0° C. for 1 hour, and then at room temperature overnight. The solvent was then distilled off under reduced pressure. The resulting solid was then washed with hexane to obtain a lithium salt of biindene.

The lithium salt of biindene thus obtained was then cooled to a temperature of −78° C. To the lithium salt was then added 100m of toluene. To the resulting suspension was then slowly added 1.14 g (4.4 mmol) of cyclopentadienylzirconium trichloride suspended in 100 m of toluene. The suspension was stirred overnight while elevating the reaction temperature to 0° C. and then the reaction temperature was slowly raised to room temperature. The suspension was further stirred at room temperature for 3 hours and then heated under reflux for 30 hours. Thereafter, the solvent was distilled off from the reaction mixture under reduced pressure and the resultant was then extracted with methylene chloride. The extract was subjected to distillation under reduced pressure to remove the solvent therefrom to obtain a yellow solid. The solid thus obtained was then recrystallized from methylene chloride/diethyl ether to obtain a yellow solid.

$^1$H-NMR spectrum (CDCl$_3$) of the solid thus obtained was as follows:

δ = 6.13   (Cp-H)
6.65–6.75  (d, 2, 3-Ind-H)
7.2–7.9    (m, aromatic-H).

This solid was identified as (biindenyl)bis(cyclopentadienylzirconium dichloride).

Figure 3:
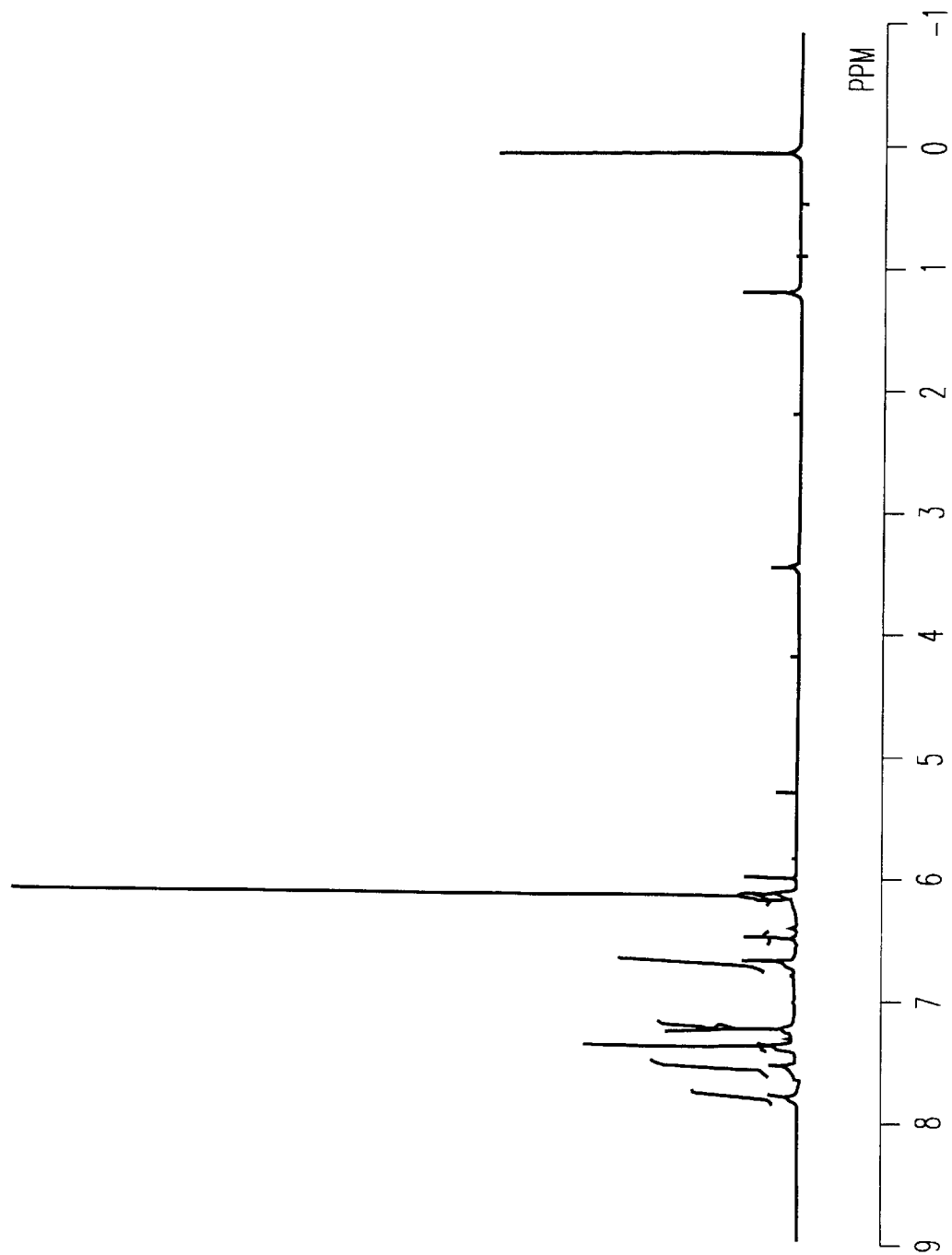
FIG. 3 illustrates $^1$H-NMR spectrum of (biindenyl)bis-(cyclopentadienylzirconium dichloride) obtained in Example 2.

¹H-NMR spectrum of this compound is shown in FIG. 3.

EXAMPLE 3

Into a 2l-autoclave were charged 500 m of toluene, 1.25 mmol (in aluminum equivalence) of methyl aluminoxane (molecular weight: 1,121; available from Toso Aczo Co., Ltd.), and 0.68 mg of (biindenyl)bis(cyclopentadienylzirconium dichloride) obtained in Example 2. The system was then allowed to undergo polymerization at a temperature of 80° C. for 30 minutes by feeding ethylene into the autoclave in such a manner that the ethylene pressure becomes 8 kg/cm²G to obtain 18.30 g of a polymer.

EXAMPLE 4

Into a 2-autoclave were charged 500 ml of toluene, 0.125 mmol of triisobutyl aluminum, 0.17 mg of (biindenyl)bis(cyclopentadienylzirconium dichloride) obtained in Example 2, and 1.0 mg of N,N-dimethyl aniliniumtetrakispentafluorophenylborate. The system was then allowed to undergo polymerization at a temperature of 80° C. for 30 minutes by feeding ethylene into the autoclave in such a manner that the ethylene pressure becomes 8 kg/cm²G to obtain 12.6 g of a polymer.

EXAMPLE 5

Into a 2l-autoclave were charged 500 ml of toluene, 15 m of hexene-1, 1.25 mmol (in aluminum equivalence) of methyl aluminoxane (molecular weight: 1,121; available from Toso Aczo Co., Ltd.), and 0.68 mg of (biindenyl)bis(cyclopentadienylzirconium dichloride) obtained in Example 2. The system was then allowed to undergo polymerization at a temperature of 80° C. for 30 minutes by feeding ethylene into the autoclave in such a manner that the ethylene pressure becomes 8 kg/cm²G to obtain 15.3 g of a polymer.

The organic transition metal compound of the present invention is novel and the use of this compound as an olefin polymerization catalyst advantageously makes it possible to efficiently produce a polyolefin.

While the invention has been described in detail and with reference to specific embodiments thereof, it will be apparent to one skilled in the art that various changes and modifications can be made therein without departing from the spirit and scope thereof.

What is claimed is:

1. An organic transition metal compound, represented by the following formula (1):

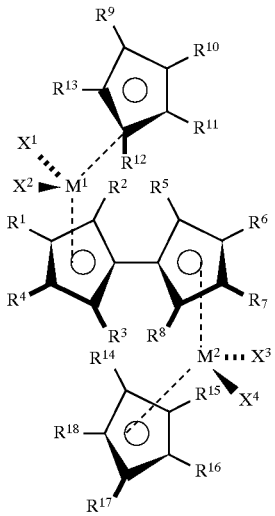

wherein $M^1$ and $M^2$, which may be the same or different from each other, each represents a transition metal atom selected from the group consisting of Ti, Zr and Hf; $R^1$, $R^2$, $R^3$, $R^4$, $R^5$, $R^6$, $R^7$ and $R^8$, which may be the same or different from each other, each represents a hydrogen atom, a $C_{1-10}$ hydrocarbon group or a $C_{1-10}$ alkylsilyl group and may be connected to each other to form rings, with the proviso that at least one of $R^1$, $R^2$, $R^3$, $R^4$, $R^5$, $R^6$, $R^7$ and $R^8$ is not a hydrogen atom; $R^9$, $R^{10}$, $R^{11}$, $R^{12}$, $R^{13}$, $R^{14}$, $R^{15}$, $R^{16}$, $R^{17}$ and $R^{18}$, which may be the same or different from each other, each represents a hydrogen atom, a $C_{1-10}$ hydrocarbon group or a $C_{1-10}$ alkylsilyl group and may be connected to each other to form rings; and $X^1$, $X^2$, $X^3$ and $X^4$, which may be the same or different from each other, each represents a hydrogen atom, a $C_{1-10}$ hydrocarbon group, a $C_{1-10}$ alkoxy group, a $C_{1-10}$ alkylamino group, a $C_{1-10}$ alkylsilyl group or a halogen atom.

2. A polymerization catalyst, comprising an organic transition metal compound of claim 1, an organic aluminum compound, and at least one compound selected from the group consisting of:

a protonic acid represented by the following formula (2):

wherein H represents a proton; $L^1$'s each independently represents a Lewis base; 1 represents a number of more than 0 to not more than 2; A represents a boron atom or a gallium atom; and $R^{19}$'s each independently represents a $C_{6-20}$ halogen-substituted aryl group;

a Lewis acid represented by the following formula (3):

wherein C represents a carbonium cation or a tropylium cation; A represents a boron atom or a gallium atom; and $R^{19}$'s each independently represents a $C_{6-20}$ halogen-substituted aryl group;

an ionized ionic compound represented by the following formula (4):

wherein D represents a cation of a metal selected from metals of the groups 1, 2, 8, 9, 10, 11 and 12 in the Periodic Table; A represents a boron atom or a gallium atom; $R^{19}$'s each independently represents a $C_{6-20}$ halogen-substituted aryl group; $L^2$'s each represents a Lewis base or a cyclopentadienyl group; and m represents a number of from not less than 0 to not more than 2; and a Lewis-acid compound represented by the following formula (5):

$$AR^{19}_3 \quad (5)$$

wherein A represents a boron atom or gallium atom; and $R^{19}$'s each independently represent a $C_{6-20}$ halogen-substituted aryl group.

3. A process for the preparation of a polyolefin, which comprises polymerizing an olefin in the presence of the polymerization catalyst of claim 2.

4. The polymerization catalyst of claim 2, wherein said organic aluminum compound is a compound represented by the following formula (8):

$$\begin{array}{c} R^{21} \\ | \\ R^{21'}-Al-R^{21''} \end{array} \quad (8)$$

wherein $R^{21}$, $R^{21'}$ and $R^{21''}$, which may be the same or different from each other, each represents a hydrogen atom, a halogen atom, an amide group, an alkoxide group or a hydrocarbon group, with the proviso that at least one of $R^{21}$, $R^{21'}$ and $R^{21''}$ is a hydrocarbon group.

5. A process for the preparation of a polyolefin, which comprises polymerizing an olefin in the presence of the polymerization catalyst of claim 4.

6. A polymerization catalyst, comprising an organic transition metal compound of claim 1 and an aluminoxane selected from the compounds represented by the following formula (6) or (7):

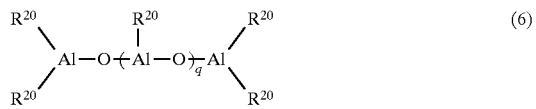

$$\begin{array}{c} R^{20} \quad R^{20} \quad R^{20} \\ \diagdown \quad | \quad \diagup \\ Al-O(-Al-O)_q-Al \\ \diagup \qquad \qquad \diagdown \\ R^{20} \qquad \qquad R^{20} \end{array} \quad (6)$$

$$\left[ -(O-Al)_{q+2} - \right] \quad (7)$$
$$\qquad \quad | \\ \qquad R^{20}$$

wherein $R^{20}$'s each independently represents a hydrogen atom, a $C_{1-20}$ alkyl group, a $C_{6-20}$ aryl, a $C_{7-20}$ arylalkyl or a $C_{7-20}$ alkylaryl group; and q represents an integer of from 2 to 50.

7. A process for the preparation of a polyolefin, which comprises polymerizing an olefin in the presence of the polymerization catalyst of claim 6.

8. A polymerization catalyst, comprising an organic transition metal compound of claim 1, an organic aluminum compound of formula 8:

$$\begin{array}{c} R^{21} \\ | \\ R^{21'}-Al-R^{21''} \end{array} \quad (8)$$

wherein $R^{21}$, $R^{21'}$ and $R^{21''}$, which may be the same or different form each other, each represents a hydrogen atom, a halogen atom, an amide group, an alkoxide group or a hydrocarbon group, with the proviso that at least one of $R^{21}$, $R^{21'}$ and $R^{21''}$ is hydrogen, and at least one compound selected from the group consisting of:

a protonic acid represented by the following formula (2):

$$[HL^1_l][AR^{19}_4] \quad (2)$$

wherein H represents a proton; $L^1$'s each independently represent a Lewis base; l represents a number of more than 0 to not more than 2; A represents a boron atom, an aluminum atom or a gallium atom; and $R^{19}$'s each independently represent a $C_{6-20}$ halogen-substituted aryl group; a Lewis acid represented by the following formula (3):

$$[C][AR^{19}_4] \quad (3)$$

wherein C represents a carbonium cation or a tropylium cation; A represents a boron atom; an aluminum atom or a gallium atom; and $R^{19}$'s each independently represent a $C_{6-20}$ halogen-substituted aryl group;

an ionized ionic compound represented by the following formula (4):

$$[DL^2_m][AR^{19}_4] \quad (4)$$

wherein D represents a cation of a metal selected from metals of the groups 1, 2, 8, 9, 10, 11 and 12 in the Periodic Table; A represents a boron atom, an aluminum atom or a gallium atom; $R^{19}$'s each independently represent a $C_{6-20}$ halogen-substituted aryl group; $L^2$'s each represent a Lewis base or a cyclopentadienyl group; and m represents a number of from not less than 0 to not more than 2; and a Lewis-acid compound represented by the following formula (5):

$$AR^{19}_3 \quad (5)$$

wherein A represents a boron atom, an aluminum atom or a gallium atom; and $R^{19}$'s each independently represent a $C_{6-20}$ halogen-substituted aryl group.

\* \* \* \* \*